United States Patent [19]

Das et al.

[11] Patent Number: 4,536,513

[45] Date of Patent: Aug. 20, 1985

[54] 7-OXABICYCLOHEPTANE SUBSTITUTED PROSTAGLANDIN INTERPHENYLENE ANALOGS USEFUL IN THE TREATMENT OF THROMBOLYTIC DISEASE

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 589,384

[22] Filed: Mar. 14, 1984

[51] Int. Cl.³ .................. A61K 31/34; A61K 31/557; C07D 307/00
[52] U.S. Cl. ..................................... 514/469; 549/463
[58] Field of Search ........................ 549/463; 424/285; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane substituted interphenylene prostaglandin ethers are provided having the structural formula

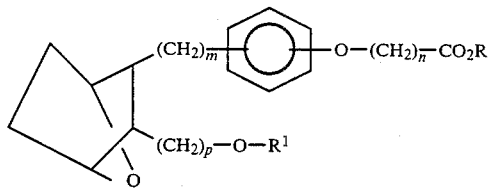

and including all stereoisomers thereof.

The compounds are cardiovascular agents useful, for example, in the treatment of thrombolytic disease.

11 Claims, No Drawings

7-OXABICYCLOHEPTANE SUBSTITUTED PROSTAGLANDIN INTERPHENYLENE ANALOGS USEFUL IN THE TREATMENT OF THROMBOLYTIC DISEASE

DESCRIPTION OF THE INVENTION

The present invention realtes to 7-oxabicycloheptane prostaglandin interphenylene ethers which are cardiovascular agents useful, for example, in the treatment of thrombolytic disease. These compounds have the structural formula

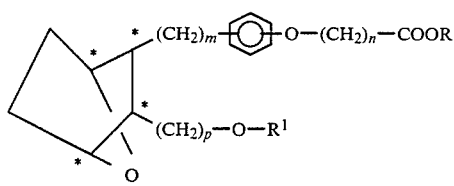

and including all stereoisomers thereof, wherein m is 1 to 4; n is 1 to 8; p is 1 to 4; R is H, lower alkyl or alkali metal; and $R^1$ is lower alkyl, aryl, aralkyl, cycloalkyl, cycloalkylalkyl or lower alkenyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or lower alkoxy groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" includes straight or branched chain radicals of from 2 to 12 carbons, preferably 2 to 6 carbons in the normal chain, which include one double bond in the normal chain, such as ethenyl, 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$", "$(CH_2)_n$" and "$(CH_2)_p$" includes a straight or branched chain radical having from 1 to 4 carbons in the normal chain in the case of "$(CH_2)_m$" and "$(CH_2)_p$" and 1 to 8 carbons in the normal chain in the case of "$(CH_2)_n$" and may contain one or more lower alkyl substituents. Examples of $(CH_2)_m$, $(CH_2)_n$ and $(CH_2)_p$ groups include $CH_2$, $CH_2CH_2$, $(CH_2)_3$, $(CH_2)_4$,

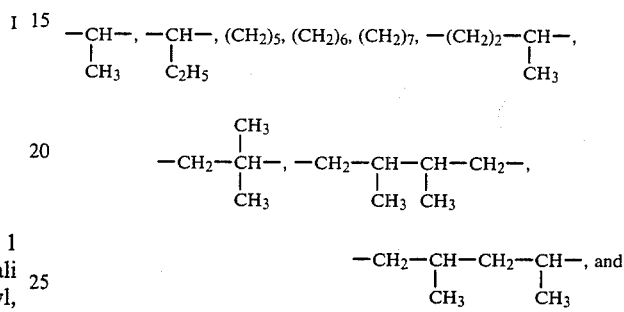

the like.

Preferred are those compounds of formula I wherein m is 1, n is 1 or 2, R is H, p is 1 and $R^1$ is lower alkyl, aryl, such as phenyl, or aralkyl such as benzyl.

The various compounds of the invention may be prepared as outlined below.

Compounds of formula I wherein m is 1 and p is 1, that is,

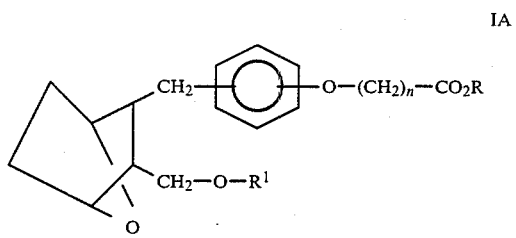

may be prepared according to the following reaction description.

The mesoanhydride

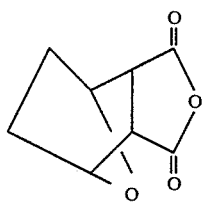

prepared as described in U.S. Pat. Nos. 4,143,054 and 4,220,594, is reduced by reaction with a reducing agent such as lithium aluminum hydride or diisobutylaluminum hydride in the presence of an inert organic solvent such as tetrahydrofuran, toluene or ether, to form the diol B

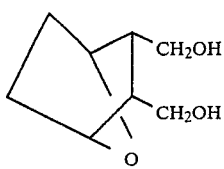

B

The diol B is then subjected to a chloroformylation reaction by reacting B with phosgene in the presence of an inert organic solvent such as tetrahydrofuran, ether or methylene chloride and an aromatic solvent such as toluene or benzene, to form alcohol C

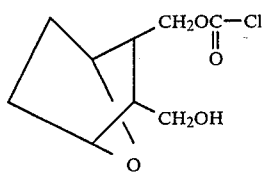

C which is converted to a cyclic-carbonate D by treating alcohol C with pyridine or other organic base, such as triethylamine or diazabicycloundecane in the presence of dichloromethane, ether or chloroform to form D

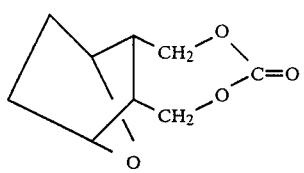

D

The cyclic-carbonate D is then reacted with an alkanol (alkyl-OH) such as isopropanol, ethanol or methanol to form the alcohol II

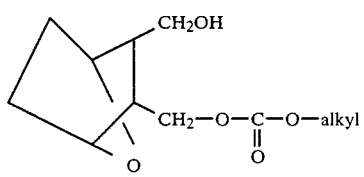

II which is then oxidized by reacting II with pyridinium chlorochromate in the presence of sodium acetate and dichloromethane to form the aldehyde III

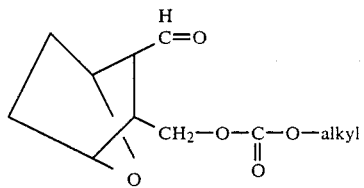

III

Aldehyde III is then subjected to a Grignard reaction by reacting same with magnesium and a halogenated aromatic derivative such as 3-bromophenylmethoxymethyl ether or other compound of the structure

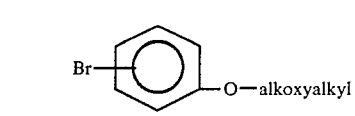

E to form a mixture of alcohol isomers

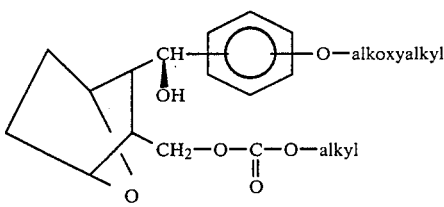

IV

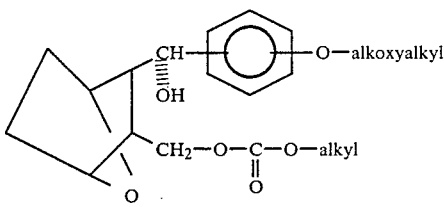

V

The isomers IV and V are separated by conventional means, such as by silica gel column chromatography, and the desired isomer is acylated by reacting same with acetic anhydride in the presence of dimethylaminopyridine and a basic organic solvent such as pyridine to form the acetates VI and VII

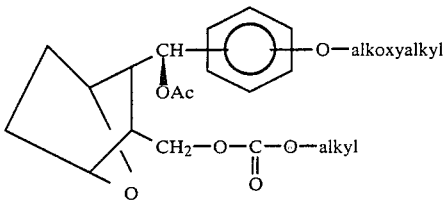

VI

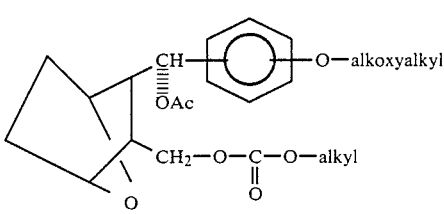

VII which are separated by column chromatography or other conventional means into the separate isomers VI and VII.

The desired isomer is then made to undergo hydrogenolysis by treating VI or VII with palladium on charcoal and hydrogen in acetic acid to form VIII

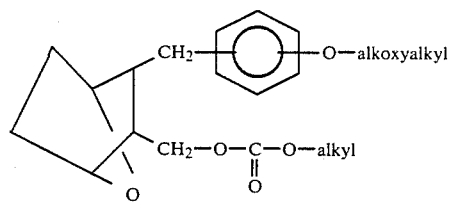  VIII

Compound VIII is then reduced by treatment with lithium aluminum hydride in the presence of an inert organic solvent such as tetrahydrofuran to form alcohol IX

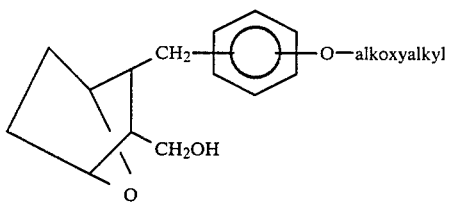  IX which is then made to undergo ether formation by reaction with a strong base such as KOH, NaOH or LiOH in the presence of an inert solvent such as xylene and then after removal of solvent, reacting with an ether compound of the structure R$^1$O-Mesyl or     F R$^1$O-Tosyl     F' or a halide of the structure

R$^1$X     F"

wherein X is Cl or Br, to form the ether X

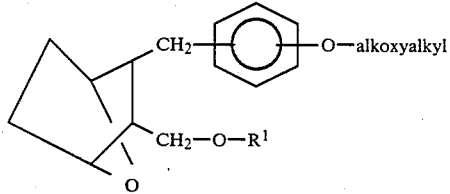  X

Ether compound X is then hydrolyzed by treatment with an acid such as HCl in the presence of an inert organic solvent such as tetrahydrofuran to form ether alcohol XI

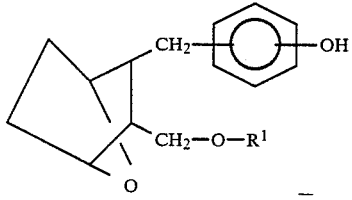  XI which is then subjected to O-alkylation by reaction with a base such as sodium hydride, potassium hydride or potassium carbonate in the presence of a haloalkanoic acid ester G Hal—(CH$_2$)$_n$—COOalkyl     G and an inert organic solvent such as dimethoxyethane to form the ester XII

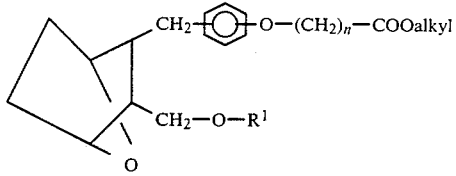  XII

The ester XII is then hydrolyzed by treatment with a base such as lithium hydroxide, potassium carbonate or sodium hydroxide in the presence of an inert organic solvent such as tetrahydrofuran, methanol or dimethoxyethane-water to form the acid XIII

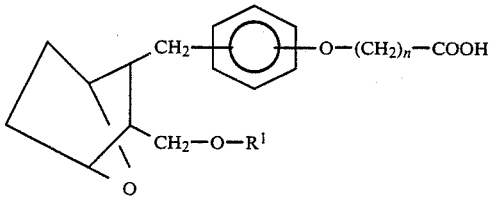  XIII

Compounds of formula I wherein m is other than 1, that is, m is 2, 3 or 4, may be prepared by subjecting aldehyde III to a homologation sequence, such as a Wittig reaction with (C$_6$H$_5$)$_3$P=CHOMe followed by hydrolysis (m−1) times. The aldehyde IIIA

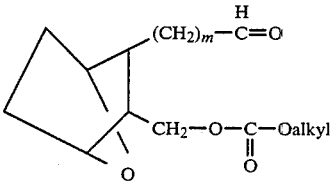  IIIA where m is 2 to 4 is thus carried on to compounds of this invention wherein m is 2 to 4 by subjecting IIIA to a Grignard reaction, acetylating the desired alcohol isomer to form the corresponding acetate, subjecting the acetate to hydrogenolysis and then reducing to form an alcohol which is esterified to form alcohol IXA

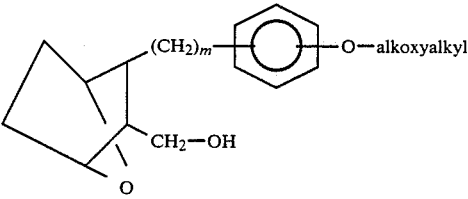  IXA

Alcohol IXA is then subjected to ether formation by reaction with F, F' or F" to form the corresponding either, which is then hydrolyzed to form an ether alochol. The either alcohol is subjected to O-alkylation to form esters and subsequently to acids of formula I where m is 2 to 4, as described above with respect to the conversion of aldehyde III and aldehyde XIII to form the compounds of the invention.

To form compounds of Formula I wherein m is 1 and p is 2 to 4, compound VIII is hydrolyzed by treatment with an acid such as HCl in the presence of an inert organic solvent such as tetrahydrofuran to form XIV

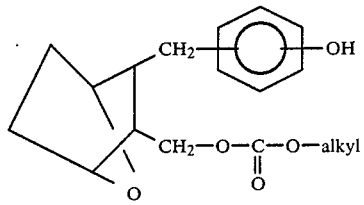

XIV which is then subjected to O-alkylation by reaction with a base such as sodium hydride, potassium hydride or potassium carbonate in the presence of a haloalkanoic acid ester Hal—$(CH_2)_n$—COOalkyl    G and an inert organic solvent such as dimethoxyethane to form the ester XV

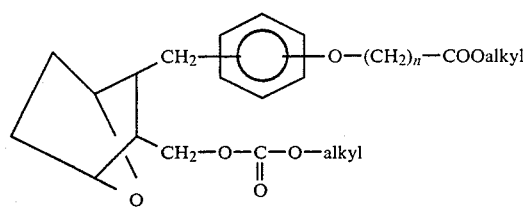

XV

The ester XV is then hydrolyzed by treatment with a base such as lithium hydroxide, potassium carbonate or sodium hydroxide in the presence of an inert organic solvent such as tetrahydrofuran, methanol or dimethoxyethane-water to form the acid XVI

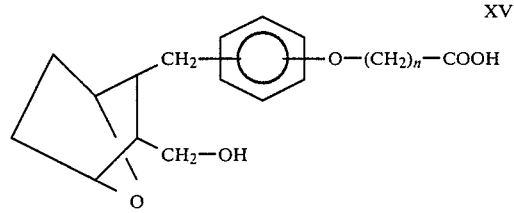

XVI

Acid XVI is then esterified by treatment with diazomethane or other diazoalkane in the presence of ether as a solvent to form the hydroxyalkyl ester XVII

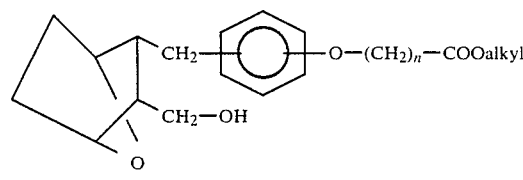

XVII

The ester XVII is then subjected to a Collins oxidation by reacting XVII with chromium trioxide in the presence of a basic solvent such pyridine and dichloromethane to form the aldehyde XVIII

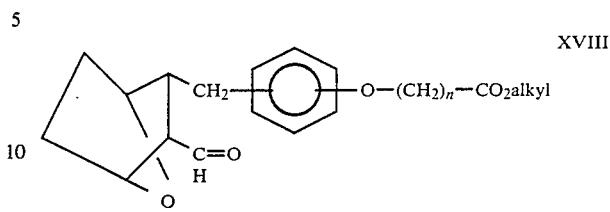

XVIII

The aldehyde XVIII is used to prepare aldehyde XIX (where p is 2-4)

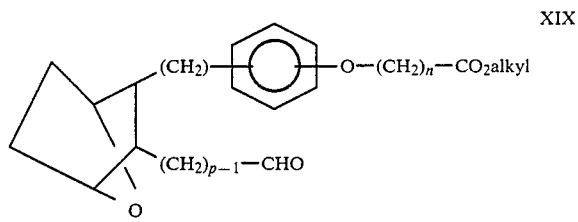

XIX by carrying out a homologation sequence, such as a Witting reaction with $(C_6H_5)_3P$=CHOMe followed by hydrolysis, (p−1) times. The aldehyde XIX (where p is 2-4) is thus carried on to compounds of this invention where p is 2-4, by reducing aldehyde XIX emloying a reducing agent such as sodium borohydride or sodium cyanoborohydride in a solvent such as methanol to form the alcohol ester XX

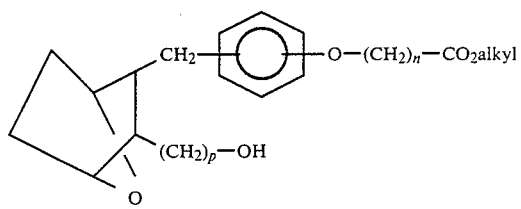

XX which is subjected to an etherification reaction with F, F′ or F″ as described above to form XXI.

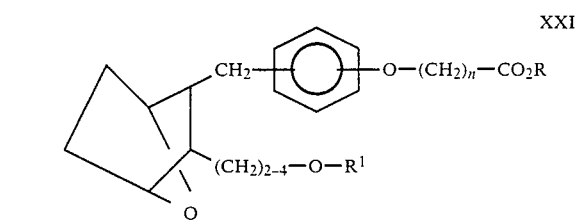

XXI

Compounds of the invention wherein m is 2, 3 or 4 and p is 2, 3 or 4 may be prepared by oxidizing alcohol IXA

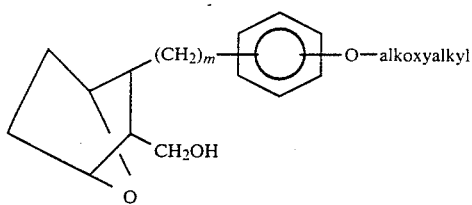

IXA with pyridinium chlorochromate in the presence of methylene chloride and sodium acetate to form aldehyde XXII

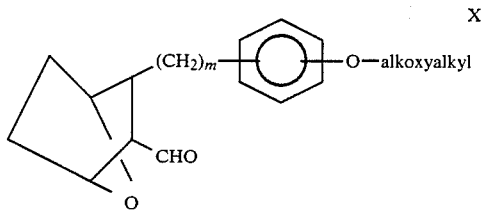

XXII

Aldehyde XXII is the subjected to a homologation sequence such as a Wittig reaction with $(C_6H_5)_3P^+Cl^-CH_2OMe$ followed by hydrolysis (p−1) times to form aldehyde XXIII

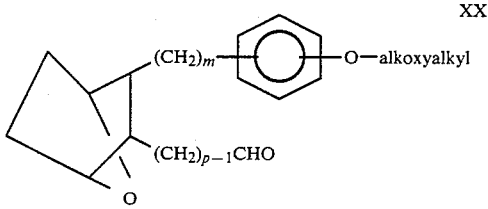

XXIII

Aldehyde XXIII is then reduced to the corresponding alcohol XXIV

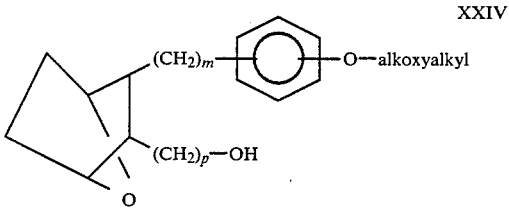

XXIV by reacting XXIII with sodium borohydride in an alcoholic solvent like methanol, ethanol or THF-methanol. alcohol XXIV may then be subjected to an etherification reaction with F, F' or F" followed by O-alkylation and hydrolysis as described hereinbefore to form the compounds of the invention.

Compounds of formula I wherein $R^1$ is aryl such as phenyl or substituted phenyl may be prepared by reacting the alcohol IX with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure

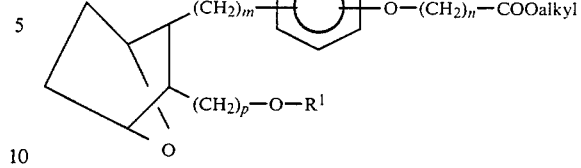

XXV wherein $R^1$ is phenyl or substituted phenyl.

The esters within the scope of formula I (that is, where R is alkyl) can be converted to the free acid, that is, to

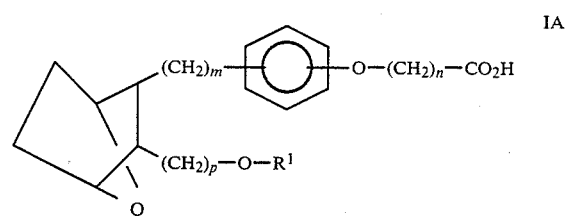

IA by treating the esters with an alkali metal hydroxide, such as lithium or sodium hydroxide to form the corresponding alkali metal salt (wherein R is an alkali metal such as Na, Li or K) followed by neutralization with an acid, such as dilute hydrochloric acid or oxalic acid to form the acid IA.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

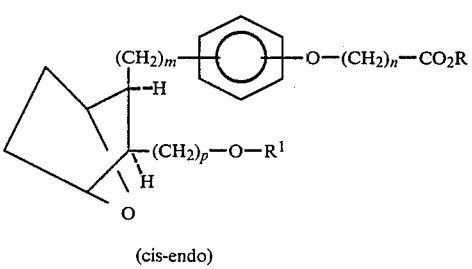

Ia (cis-endo)

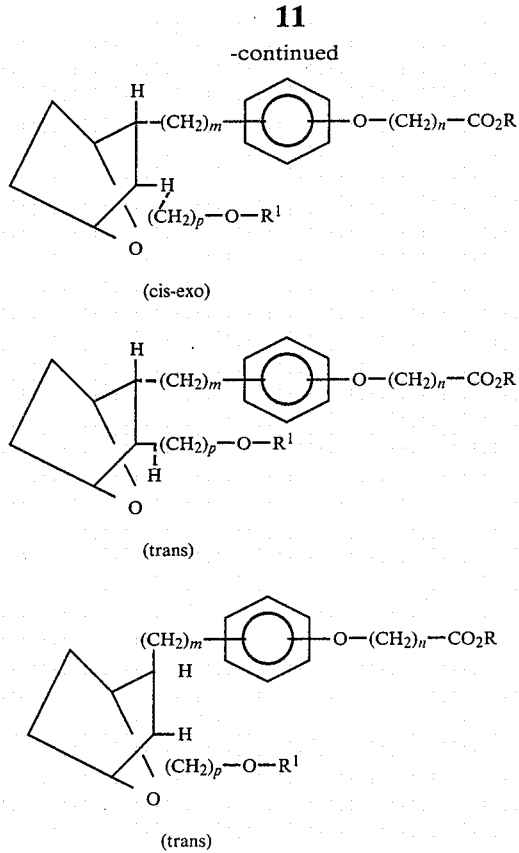

(cis-exo)       Ib (trans)         Ic (trans)         Id

The nucleus in each of the compounds of the invention is depicted as

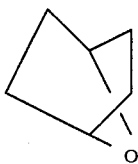

for matter of convenience; it will also be appreciated that the nucleus in the compounds of the invention may be depicted as

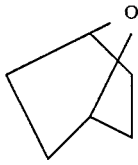

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting broncho-constriction as induced by asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors. In addition, the compounds of the invention are useful as analgesic agents in the manner of aspirin and indomethacin in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swellling, tenderness, pain and stiffnes in conditions such as rheumatoid arthritis.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

(1α,2β,3β,4α)-[3-[[3-[(Hexyloxy)methyl]-7-oxabicyclo[2.2.1]hept-2-yl]methyl]phenoxy]acetic acid, ethyl ester

A (1α,2β,3β,4α)-Cis-exo-7-oxabicyclo[2.2.1]heptane-2,3-dimethanol

To a suspension of 11.4 g lithium aluminum hydride (300 mmole, 1.6 eq.) in 400 ml of dry THF at 0° C. was added dropwise a solution of 32 g cis-exo-hexahydro-4,7-epoxyisobenzofuran-1,3-dione(mesoanhydride) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B. (1α,2β,3β,4α)-Cis-exo-2-hydroxymethyl 3-chlorooxycarbonyloxymethyl-7-oxabicyclo[2.2.1-]heptane and

C.

(1α,2β,3β,4α)-cis-exo-7-oxabicyclo[2.2.1]heptane-2,3-dimethanol carbonate

To a solution of 10 g title A diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give title B compound as a crude oil.

This oil was dissolved in 30 ml of dry $CH_2Cl_2$ and cooled to $-50°$ C. To this solution was added dropwise a solution of 10 ml pyridine in 10 ml $CH_2Cl_2$. It was stirred for 10 minutes and quenched with $H_2O$. The mixture was extracted thoroughly with $CH_2Cl_2$. The organic extract was dried over $MgSO_4$ and concentrated to give the title C cyclic carbonate as a crystalline solid (10.7 g).

D.
(1α,2β,3β,4α)-Cis-exo-2-hydroxymethyl-3-isopropyloxycarbonyloxymethyl-7-oxabicyclo[2.2.1]heptane A mixture of 10.7 g title C cyclic carbonate (58.1 mmole) in 100 ml isopropanol was refluxed for 24 hours. Excess isopropanol was removed under reduced pressure to give 14.4 g title D hydroxycarbonate as a viscous oil.

E.
(1α,2β,3β,4α)-Cis-exo-2-formyl-3-isopropyloxycarbonyloxymethyl-7-oxabicyclo[2.2.1]heptane To 5.0 g of title D alcohol (20.6 mmol) in 65 ml of dry $CH_2Cl_2$ at 25° C. was added 13.2 Celite, 1.7 g NaOAc (6.15 mmole, 30 mole %) and 13.2 g pyridinium chlorochromate (61.5 mmole, 3 eq.). The mixture was stirred at 25° C. for 2 hours then diluted with 100 ml ether and filtered through a bed of fluorosil. The filtrate was concentrated to give 3.8 g of title E aldehyde as a clear oil which was used in the next reaction without further purification (78%)

F.
[1α,2β(1R),3β,4α]-[3-[[(3-Isopropyloxycarbonyloxymethyl)-7-oxabicyclo[2.2.1]hept-2-yl]hydroxymethyl]-phenyl]-methoxymethyl ether and

G.
[1α,2β(1S),3β,4α]-[3-[[(3-Isopropyloxycarbonyloxymethyl)-7-oxabicyclo[2.2.1]hept-2-yl]hydroxymethyl]-phenyl]methoxymethyl ether To 498.1 mg of magnesium turnings (20.5 mmole, 3 eq.) in 30 ml of dry THF at 45° C. was added 4.4 g 3-bromophenylmethoxymethylether and a crystal of iodine. The mixture was stirred at 45° C.–50° C. for 4 hours.

To a solution of 3.8 g title E aldehyde (15.7 mmole) in 20 ml of dry THF at $-78°$ C. was added the above Grignard solution through a canula. The mixture was stirred at $-78°$ C. under argon for 1.5 hours, quenched with saturated $NH_4Cl$ solution and the layers were separated. The aqueous layer was extracted with three 50 ml portions of $CH_2Cl_2$. The combined organic layer was dried over anhydrous $MgSO_2$ and concentrated to give a crude mixture which was separated on a silica gel column, eluting with 50% ether in hexanes to give 1.9 g of title F isomer and 800 mg of title G isomer.

H.
[1α,2β(1R),3β,4α]-[3-[[(3-Isopropyloxycarbonyloxymethyl)-7-oxabicyclo[2.2.1]hept-2-yl]acetoxymethyl]-phenyl]methoxymethyl ether To 1.9 g of title F alcohol (5 mmole) in 50 ml of pyridine was added 2.5 g acetic anhydride (25 mmole, 5 eq.) and a catalytic amount of 4-dimethylaminopyridine. The mixture was stirred at 25° C. for 1 hour and then concentrated. The residue was purified on a silica gel column eluting with 40% ether in hexanes to give 1.4 g title H acetate as a white solid (66.3%).

I.
(1α,2β,3β,4α)-[3-[[(3-Isopropyloxycarbonyloxymethyl)-7-oxabicyclo[2.2.1]hept-2-yl]methyl]phenyl]methoxymethyl ether A mixture of 1.2 g title H benzylacetate and 1.2 g of 10% palladium over carbon in 30 ml of acetic acid was shaken in a Parr bottle under 40 psi hydrogen pressure at 25° C. for 24 hours. TLC showed about 30% completion. The product and unreacted starting material were separated on a silica gel column, eluting with 30% ether in hexane. The unreacted starting material was again subjected to hydrogenolysis under the same conditions. Total yield: 520 mg of title I compound.

J.
(1α,2β,3β,4α)-[3-[[3-Hydroxymethyl-7-oxabicyclo[2.2.1]hept-2-yl]methyl]phenyl]methoxmethyl ether To a slurry of 8.1 mg of lithium aluminum hydride (0.25 mmole, 54 eq.) in 2 ml of dry THF at 0° C. was added a solution of 90 mg of title I carbonate (0.25 mmole) in 2 ml of dry THF. After stirring at 0° C. for 5 hours, a solution of saturated sodium sulfate was added dropwise to the reaction mixture until no more white precipitates formed. 30 ml of $CH_2Cl_2$ along with anhydrous $MgSO_4$ was added and the mixture was stirred for 30 minutes and filtered. The filtrate was concentrated to give 70 mg of title alcohol.

K.
(1α,2β,3β,4α)-[3-[[(Hexyloxy)methyl]-7-oxabicyclo[2.2.1]hept-2-yl]methyl]phenyl]methoxymethyl ether To a solution of 103 mg of powered potassium hydroxide (2.5 mmole, 10 eq.) in 10 ml of dry xylene was added a solution of 70 mg of title J alcohol (0.25 mmole) in 10 ml of dry xylene. The mixture was heated to reflux and 10 ml of xylene was distilled off.

To the cooled remaining solution was added 405 mg of hexyl mesylate (2.5 mmole, 10 eq.). The mixture was refluxed for 2 hours, then cooled to 25° C. and diluted with 100 ml of ether. The ethereal solution was washed with two 30 ml portions of $H_2O$, dried over anhydrous $MgSO_4$ and concentrated. The residue was purified on a silica gel column, eluting with 15% EtOAc/hexane to give 110 mg of a mixture of title ether and hexylmesylate.

L.
(1α,2β,3β,4α)-[3-[[(Hexyloxy)methyl]-7-oxabicyclo[2.2.1]hept-2-yl]methyl]phenol To a solution of 110 mg of crude title K ether (ca. 0.25 mmole) in 20 ml of THF was added 5 ml of a 4N HCl solution. After stirring at 25° C. for 20 hours the mixture was concentrated, diluted with 10 ml of $H_2O$, basified with solid $NaHCO_3$ and extracted with three 20 ml portions of $CH_2Cl_2$. The combined organic layers were dried over anhydrous $MgSO_4$ and concentrated. The residue was purified on a silica gel column, eluting with 20% EtOAc/hexane to give 73 mg of title phenol as an oil.

M.

(1α,2β,3β,4α)-[3-[[3-[Hexyloxy)methyl-7-oxabicyclo[2.2.1]hept-2-yl]methyl]phenoxy]acetic acid, ethyl ester To a slurry of 32.8 mg of prewashed sodium hydride (50% dispersion in mineral oil, 0.44 mmole, 2 eq.) in 3 ml of dry dimethoxyethane (DME) at 0° C. was added a solution 73 mg of title L phenol in 2 ml of DME (0.22 mmole). After stirring at 0° C. for 30 minutes, 97.4 mg of ethyl bromoacetate (0.66 mmole, 3 eq.) was added. The mixture was warmed to 25° C., stirred for 2 hours, diluted with 50 ml of ether and filtered. The filtrate was concentrated and the residue was purified on a silica gel column eluting with 25% EtOAc/hexane to give 70 mg of title compound as an oil.

EXAMPLE 2

(1α,2β,3β,4α)-[3-[[3-[(Hexyloxy)methyl]-7-oxabicyclo[2.2.1]hept-2-yl]methyl]phenoxy]acetic acid To 70 mg of the Example 1 ester (0.17 mmole) in 8 ml of THF and 2 ml of $H_2O$ at 0° C. was added dropwise 1.7 ml of a 1M lithium hydroxide solution. After stirring at 25° C. for 2 hours, the mixture was concentrated, diluted with 10 ml of $H_2O$, acidified to pH 3 with a saturated oxalic acid solution and extracted with three 20 ml portions of ether. The combined ethereal extract was washed with two 10 ml portions of $H_2O$, dried over anhydrous $MgSO_4$ and concentrated.

The residue was purified on a CC-7 silica gel column, eluting with a gradient of pentane/ether. The product was kept under high vaccum for one day to give 25 mg of title product as a yellow oil. TLC: silica gel; 10% $MeOH/CH_2Cl_2+0.1\%$ AcOH; $R_f \sim 0.35$.

Anal Calcd for $C_{22}H_{32}O_5$: C, 70.18; H, 8.56. Found: C, 70.14; H, 8.37

EXAMPLE 3

(1α,2β,3β,4α)-[3-[[3-[(Hexyloxy)methyl]-7-oxabicyclo[2.2.1]hept-2-yl]methyl]phenoxy]propionic acid Following the procedure of Examples 5, 1 and 2, except substituting ethylbromopropionate for ethylbromoacetate, the title compound is obtained.

EXAMPLE 4

(1α,2β,3β,4α)-3-[[3-[(Hexyloxy)methyl]-7-oxabicyclo[2.2.1]hept-2-yl]ethyl]phenoxy]acetic acid

A.

(1α,2β,3β,4α)-[Cis-exo-3-isopropyloxycarbonyloxymethyl-7-oxabicyclo[2.2.1]hept-2-yl]acetaldehyde Into a dry 1000 ml round bottom 3-necked flask containing a stir bar is added dried 12.9 g (37.7 mmoles) methoxymethyltriphenylphosphonium chloride (($C_6H_5)_3P^+$—$CH_2OCH_3Cl^-$) and 235 ml distilled toluene (stored over molecular sieves). The resulting suspension is stirred in an ice-bath, under argon, until cold and then a 1.55 M solution of 18.3 ml (28.3 mmol) of potassium t-amylate in toluene is added dropwise. A bright red solution forms which is stirred at 0° C. for an additional 35 minutes. Thereafter, a solution of 4.55 g (18.8 mmol) of Example 1 title E aldehyde in 60 ml toluene is added by means of a dropping funnel over a 35 minute period with the ice-bath still in place. The reaction is then quenched by addition of 2.3 g (39 mmol) acetic acid in 5 ml ether. The reaction mixture immediately turns pale yellow and is immediately poured into 200 ml saturated $NH_4Cl$, and extracted with ether (4×200 ml). The combined ether phases are washed with NaCl, saturated solution, and dried ($MgSO_4$) and concentrated to yield an oil in a white crystalline solid (phosphine oxide). The reaction mixture is triturated with ether and the precipitated phosphine oxide is filtered off. Ether solution is concentrated under reduced pressure, dissolved in THF and treated with 10%, aqueous hydrochloric acid solution. After stirring for one hour at room temperature, solid sodium bicarbonate is added to the reaction mixture. The THF solution is dried over anhydrous magnesium sulfate and concentrated under reduced pressure. The crude residue is purified on a LPS-1 silica gel column with ethyl acetate in hexane to obtain the title A aldehyde.

B.

(1α,2β,3β,4α)-[3-[[3-[(Hexyloxy)methyl]-7-oxabicyclo[2.2.1]hept-2-yl]ethyl]phenoxy]acetic acid Following the procedure of Examples 1, Parts F-M, and 2 except substituting the above part A aldehyde for the aldehyde of Example 1, Part E, the title compound is obtained.

EXAMPLE 5

(1α,2β,3β,4α)-[3-[[3-[(Hexyloxy)methyl]-7-oxabicyclo[2.2.1]hept-2-yl]propyl]phenoxy]acetic acid

A.

(1α,2β,3β,4α)-[Cis-exo-3-isopropyloxycarbonyloxymethyl-7-oxabicyclo[2.2.1]-hept-2-yl]propionaldehyde Following the procedure of Example 4, Part A except substituting the Example 4, title A compound with Example 1 title E aldehyde, the title aldehyde is obtained.

B.

(1α,2β,3β,4α)-[3-[[3-(Hexyloxy)methyl]-7-oxabiclo[2.2.1]hept-2-yl]propyl]phenoxy]acetic acid Following the procedure of Examples 1 and 2 except substituting the title A aldehyde for the aldehyde of Example 1, Part E, the title compound is obtained.

EXAMPLE 6

(1α,2β,3β,4α)-[3-[[3-[(Benzyloxy)methyl]-7-oxabicyclo[2.2.1]hept-2-yl]methyl]phenoxy]butanoic acid Following the procedure of Examples 1 and 2 except substituting ethylbromobutanoate for ethylbromoacetate and substituting benzyl tosylate for hexyl mesylate, the title compound is obtained.

EXAMPLE 7

(1α,2β,3β,4α)-[3-[[3-[(Cyclohexylmethyloxy)methyl]-7-oxabicyclo[2.2.1]hept-2-yl]methyl]phenoxy]pentanoic acid Following the procedure of Examples 1 and 2 except substituting ethylbromopentanoate for ethylbromoacetate and substituting cyclohexylmethyl mesylate for hexyl mesylate, the title compound is obtained.

EXAMPLE 8

(1α,2β,3β,4α)-[3-[[3-[(Phenyloxy)methyl]-7-oxabicyclo[2.2.1]hept-2-yl]methyl]phenoxy]heptanoic acid Following the procedure of Examples 1 and 2 except substituting ethylbromoheptanoate for ethylbromoacetate and substituting phenylmesylate for hexylmesylate, the title compound is obtained.

EXAMPLE 9

(1α,2β,3β,4α)-[3-[[3-[(2-Butenyloxy)methyl]-7-oxabicyclo[2.2.1]hept-2-yl]methyl]phenoxy]hexanoic acid Following the procedure of Examples 1 and 2 except substituting ethylbromohexanoate for ethylbromoacetate and substituting 2-butenylmesylate for hexylmesylate, the title compound is obtained.

EXAMPLE 10

(1α,2β,3β,4α)-[3-[[3-[(3-Butenyloxy)methyl]-7-oxabicyclo[2.2.1]hept-2-yl]methyl]phenoxy]octanoic acid Following the procedure of Examples 1 and 2 except substituting ethylbromooctanoate for ethylbromoacetate and substituting 3-butenylmesylate for hexylmesylate, the title compound is obtained.

EXAMPLE 11

(1α,2β,3β,4α)-[4-[[3-[(1-Pentenyloxy)methyl]-7-oxabicyclo[2.2.1]hept-2-yl]methyl]phenoxy]acetic acid Following the procedure of Examples 1 and 2 except substituting 4-bromophenylmethoxymethyl ether for 3-bromophenylmethoxymethyl ether and substituting 1-pentenylmesylate for hexylmesylate, the title acid is obtained.

EXAMPLE 12

(1α,2β,3β,4α)-[2-[[3-[(Cycloheptyloxy)methyl]-7-oxabicyclo[2.2.1]hept-2-yl]methyl]phenoxy]acetic acid Following the procedure of Examples 1 and 2 except substituting 2-bromophenylmethoxymethyl ether for 3-bromophenylmethoxymethyl ether and substituting cycloheptylmesylate for hexylmesylate, the title acid is obtained.

EXAMPLE 13

(1α,2β,3β,4α)-[2-[[3-[(Pentyloxy)methyl]-7-oxabicyclo[2.2.1]hept-2-yl]methyl]phenoxy]acetic acid Following the procedure of Examples 1 and 2 except substituting 2-bromophenylmethoxymethyl ether for 3-bromophenylmethoxymethyl ether and substituting pentyl tosylate for hexyl mesylate, the title acid is obtained.

EXAMPLE 14

(1α,2β,3β,4α)-[3-[[3-[(Hexyloxy)methyl]-7-oxabicyclo[2.2.1]hept-2-yl]ethyl]phenoxy]butanoic acid Following the procedure of Examples 4, 1 and 2 except substituting ethylbromobutanoate for ethylbromoacetate, the title acid is obtained.

EXAMPLE 15

(1α,2β,3β,4α)-[3-[[3-[(Hexyloxy)methyl]-7-oxabicyclo[2.2.1]hept-2-yl]ethyl]phenoxy]pentanoic acid Following the procedure of Examples 4, 1 and 2 except substituting ethylbromopentanoate for ethylbromoacetate, the title acid is obtained.

EXAMPLE 16

(1α,2β,3β,4α)-[3-[[3-[(Phenyloxy)methyl]-7-oxabicyclo[2.2.1]hept-2-yl]ethyl]phenoxy]acetic acid Following the procedure of Examples 4, 1 and 2 except substituting phenylmesylate for hexylmesylate, the title acid is obtained.

EXAMPLE 17

(1α,2β,3β,4α)-[3-[[3-[(Cyclohexyloxy)methyl]-7-oxabicyclo[2.2.1]hept-2-yl]ethyl]phenoxy]butanoic acid Following the procedure of Examples 4, 1 and 2 except substituting ethylbromopentanoate for ethylbromoacetate and substituting cyclohexyltosylate for hexylmesylate, the title acid is obtained.

EXAMPLE 18

(1α,2β,3β,4α)-[3-[[3-[(Benzyloxy)methyl]-7-oxabicyclo[2.2.1]hept-2-yl]ethyl]phenoxy]pentanoic acid Following the procedure of Examples 4, 1, and 2, except substituting ethylbromopentanoate for ethylbromoacetate and substituting benzylmesylate and hexyl mesylate, the title acid is obtained.

EXAMPLE 19

(1α,2β,3β,4α)-[3-[[3-[(2-Propenyloxy)methyl]-7-oxabicyclo[2.2.1]hept-2-yl]ethyl]phenoxy]acetic acid Following the procedure of Examples 4, 1 and 2 except substituting 2-propenylmesylate for hexylmesylate, the title acid is obtained.

EXAMPLE 20

(1α,2β,3β,4α)-[3-[[3-[(Cyclopentylmethyloxy)methyl]-7-oxabicyclo[2.2.1]hept-2-yl]methyl]phenoxy]acetic acid Following the procedure of Examples 1 and 2 except substituting cyclopentylmethyl tosylate for hexylmesylate, the title compound is obtained.

EXAMPLE 21

(1α,2β,3β,4α)-[3-[[3-[(Hexyloxy)methyl]-7-oxabicyclo[2.2.1]hept-2-yl]butyl]phenoxy]acetic acid

A.

(1α,2β,3β,4α)-[Cis-exo-3-isopropyloxycarbonyloxymethyl-7-oxabicyclo[2.2.1]hept-2-yl]butyraldehyde Following the procedure of Example 4, part A, except substituting Example 5, part A aldehyde (prepared in Example 4, part A) for the Example 1, part E aldehyde, the title aldehyde is obtained.

B.

(1α,2β,3β,4α)-[3-[[3-[(Hexyloxy)methyl]-7-oxabicyclo[2.2.1]hept-2-yl]butyl]phenoxy]acetic acid Following the procedure of Example 4, part B, except substituting the aldehyde from part A above, for Example 5, part A aldehyde, the title aldehyde is obtained.

EXAMPLE 22

(1α,2β,3β,4α)-[3-[[3-[(Hexyloxy)methyl]-7-oxabicyclo[2.2.1]hept-2-yl]butyl]phenoxy]butanoic acid Following the procedure of Examples 21, 1 and 2, except substituting ethylbromobutanoate for ethylbromoacetate, the title acid is obtained.

EXAMPLE 23

(1α,2β,3β,4α)-[3-[[3-[2-(Hexyloxy)ethyl]-7-oxabicyclo[2.2.1]hept-2-yl]methyl]-phenoxy]acetic acid, methyl ester

A.

(1α,2β,3β,4α)-Cis-exo-7-oxabicyclo[2.2.1]heptane-2,3-dimethanol

To a suspension of 11.4 g lithium aluminum hydride (300 mmole, 1.6 eq.) in 400 ml of dry THF at 0° C. was added dropwise a solution of 32 g cis-exo-hexahydro-4,7-epoxyisobenzofuran-1,3-dione (mesoanhydride) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B. (1α,2β, 3β, 4α)-Cis-exo-2-hydroxymethyl-3-chlorooxycarbonyloxymethyl-7-oxabicyclo[2.2.1]heptane and

C. (1α,2β,3β, 4α)-Cis-exo-7-oxabicyclo[2.2.1]heptane-2,3-dimethanol carbonate To a solution of 10 g title A diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give title B compound as a crude oil.

This oil was dissolved in 30 ml of dry $CH_2Cl_2$ and cooled to −50° C. To this solution was added dropwise a solution of 10 ml pyridine in 10 ml $CH_2Cl_2$. It was stirred for 10 minutes and quenched with $H_2O$. The mixture was extracted thoroughly with $CH_2Cl_2$. The organic extract was dried over $MgSO_4$ and concentrated to give the title C cyclic carbonate as a crystalline solid (10.7 g).

D. (1α, 2β,3β,4α)-Cis-exo-2-hydroxymethyl-3-isopropyloxycarbonyloxymethyl-7-oxabicyclo[2.2.1]heptane A mixture of 10.7 g title C cyclic carbonate (58.1 mmole) in 100 ml isopropanol was refluxed for 24 hours. Excess isopropanol was removed under reduced pressure to give 14.4 g title D hydroxycarbonate as a viscous oil.

E. (1α, 2β, 3β, 4α)-Cis-exo-2-formyl-3-isopropyloxycarbonyloxymethyl-7-oxabicyclo[2.2.1]heptane To 5.0 g of title D alcohol (20.5 mmol) in 65 ml of dry $CH_2Cl_2$ at 25° C. was added 13.2 g Celite, 1.7 g NaOAc (6.15 mmole, 30 mole %) and 13.2 g pyridinium chlorochromate (61.5 mmole, 3 eq.). The mixture was stirred at 25° C. for 2 hours then diluted with 100 ml ether and filtered through a bed of fluorosil. The filtrate was concentrated to give 3.8 g of title E aldehyde as a clear oil which was used in the next reaction without further purification (78%).

F. [1α,2β(1R),3β,4α]-[3-[[(3-Isopropyloxycarbonyloxymethyl)-7-oxabicyclo[2.2.1]hept-2-yl]hydroxymethyl]-phenyl]methoxymethyl ether and

G. [1α,2β(1S),3β,4α]-[3-[[(3-Isopropyloxycarbonyloxymethyl)-7-oxabicyclo[2.2.1]hept-2-yl]hydroxymethyl]-phenyl]methoxymethyl ether To 498.1 mg of magnesium turnings (20.5 mmole, 3 eq.) in 30 ml of dry THF at 45° C. was added 4.4 g 3-bromophenylmethoxymethylether and a crystal of iodine. The mixture was stirred at 45° C.–50° C. for 4 hours.

To a solution of 3.8 g title E aldehyde (15.7 mmole) in 20 ml of dry THF at −78° C. was added the above Grignard solution through a canula. The mixture was stirred at −78° C. under argon for 1.5 hours, quenched with saturated $NH_4Cl$ solution and the layers were separated. The aqueous layer was extracted with three 50 ml portions of $CH_2Cl_2$. The combined organic layer was dried over anhydrous $MgSO_4$ and concentrated to give a crude mixture which was separated on a silica gel column, eluting with 50% ether in hexanes to give 1.9 g of title F isomer and 800 mg of title G isomer.

H. [1α,2β(1R),3β,4α]-[3-[[(3-Isopropyloxycarbonyloxymethyl)-7-oxabicyclo[2.2.1]hept-2-yl]acetoxymethyl]-phenyl]methoxymethyl ether To 1.9 g of title F alcohol (5 mmole) in 50 ml of pyridine was added 2.5 g acetic anhydride (25 mmole, 5 eq.) and a catalytic amount of 4-dimethylaminopyridine. The mixture was stirred at 25° C. for 1 hour and then concentrated. The residue was purified on a silica gel column eluting with 40% ether in hexanes to give 1.4 g title H acetate as a white solid (66.3%).

I. (1α, 2β,3β,4α)-[3-[[(3-Isopropyloxycarbonyloxymethyl)-7-oxabicyclo[2.2.1]hept-2-yl]methyl]phenyl]methoxymethyl ether A mixture of 1.2 g title H benzylacetate and 1.2 g of 10% palladium over carbon in 30 ml of acetic acid was shaken in a Parr bottle under 40 psi hydrogen pressure at 25° C. for 24 hours. TLC showed about 30% completion. The product and unreacted starting material were separated on a silica gel column, eluting with 30% ether in hexane. The unreacted starting material was again subjected to hydrogenolysis under the same conditions. Total yield: 520 mg of title I compound.

J. (1α,2β,3β,4α)-[3-[[(3-Isopropyloxycarbonyloxymethyl)-7-oxabicyclo[2.2.1]hept-2-yl]methyl]phenol A mixture of 420 mg title I compound (1.43 mmole), 10 ml of 1N HCl and 10 ml THF was stirred at 25° C. for 48 hours. The mixture was neutralized by solid $NaHCO_3$ and extracted with three 50 ml portions of $CH_2Cl_2$, dried over $MgSO_4$ and concentrated to give 480 mg of title J compound in the form of a crude oil which was used directly in the next step.

K. (1α, 2β,3β,4α)-[3-[[(3-Isopropyloxycarbonyloxymethyl)-7-oxabicyclo[2.2.1]hept-2-yl]methyl]phenoxy]acetic acid, ethyl ester To a slurry of 39.7 mg of prewashed sodium hydride (1.6 mmole, 1.1 eq.) in 3 ml dimethoxy ether (DME) at 0° C. was added a solution of 480 mg title J compound (1.5 mmole) in 2 ml DME. The mixture was stirred at 0° C. for 15 minutes. To this mixture at 0° C. was added 375 mg of ethylbromoacetate (2.25 mmole, 1.5 eq.). The reaction mixture was warmed to 25° C. and stirred for an additional 20 minutes, then diluted with 30 ml ether, and filtered. The filtrate was concentrated and purified on a silica gel column eluting with 40% ether in hexanes to give 420 mg of title K compound as an oil.

L. (1α,2β,3β,4α)-[3-[[3-Hydroxymethyl-7-oxabicyclo[2.2.1]hept-2-yl]methyl]phenoxy]acetic acid and

M. (1α,2β,3β,4α)-[3-[[3-Hydroxymethyl-7-oxabicyclo[2.2.1]hept-2-yl]methyl]phenoxy]acetic acid, methyl ester To 420 mg of title K compound (1.03 mmole) in 2 ml H$_2$O and 8 ml THF at 0° C. was added 10 ml of 1N LiOH solution. The mixture was stirred while being warmed to 25° C. over a 3 hour period. THF was evaporated. The aqueous layer containing title L compound was extracted with three 10 ml portions of ether, then acidified to pH 3 with saturated oxalic acid, saturated with solid NaCl and extracted with three 20 ml portions of CH$_2$Cl$_2$. The extract was dried over MgSO$_4$ and concentrated to give a foam which was treated directly with excess CH$_2$N$_2$ in ether to give 260 mg of title M alcohol ester as an oil.

N. (1α,2β,3β,4α)-[3-[[3-Formyl-7-oxabicyclo[2.2.1]hept-2-yl]methyl]phenoxy]acetic acid, methyl ester To 1.3 ml pyridine (8.5 mmole, 10 eq.) in 30 ml CH$_2$Cl$_2$ at 25° C. was added 850 mg chromium trioxide (8.5 mmole, 10 eq.). The mixture was stirred for 30 minutes at 25° C. To this mixture was added a solution of 260 mg title M compound (0.85 mmole) in 5 ml CH$_2$Cl$_2$. The reaction mixture was stirred for 30 minutes then diluted with 100 ml ether, filtered through a bed of fluorosil and the filtrate concentrated to give 170 mg of title N aldehyde as an oil.

O. (1α,2β,3β,4α)-[3-[[3-(2-Oxo)ethyl]-7-oxabicyclo[2.2.1]hept-2-yl]methyl]phenoxy]acetic acid, methyl ester Following the procedure of Example 4, part A, except substituting the Example 23, Part N, aldehyde for the Example 1, Part E, aldehyde, the title aldehyde compound is obtained.

P. (1α,2β,3β,4α)-[3-[[3-(2-Hydroxyethyl)]-7-oxabicyclo[2.2.1]hept-2-yl]methyl]phenoxy]acetic acid, methyl ester The aldehyde (0.95 g, 3 mmol) from part O in methanol (50 ml) was treated with NaBH$_4$ (0.19 g, 5 mmol) in an argon atmosphere at 0° C. After stirring at 0° for 1 hour, the reaction was quenched by addition of 2N HCl (to pH 2). The methanol was removed in vacuo and the reaction mixture was taken up in ether. The ether solution was washed with saturated KHCO$_3$, saturated NaCl and dried (MgSO$_4$). The ether was evaporated to yield the title P compound.

Q. (1α,2β,3β,4α)-[3-[[3-[2-(Hexyloxy)ethyl]-7-oxabicyclo[2.2.1]-hept-2-yl]methyl]phenoxyl]acetic acid Following the procedure of Example 1 parts K–M and Example 2 except substituting the above part P alcohol for the Example 1, part J alcohol, the title compound is obtained.

EXAMPLE 24

(1α,2β,3β,4α)-[3-[[3-[2-(Benzyloxy)ethyl]-7-oxabicyclo[2.2.1]hept-2-yl]methyl]phenoxy]butanoic acid Following the procedure of Examples 23, 1 and 2 except substituting ethylbromobutanoate for ethylbromoacetate and substituting benzyl tosylate for hexyl mesylate, the title compound is obtained.

EXAMPLE 25

(1α,2β,3β,4α)-[3-[[3-[2-(Cyclopentylmethyloxy)ethyl]-7-oxabicyclo[2.2.1]hept-2-yl]methyl]phenoxy]pentanoic acid Following the procedure of Examples 23, 1 and 2 except substituting ethylbromopentanoate for ethylbromoacetate and substituting cyclopentylmethyl mesylate for hexyl mesylate, the title compound is obtained.

EXAMPLE 26

(1α,2β,3β,4α)-[3-[[3-[2-(Phenyloxy)ethyl]-7-oxabicyclo[2.2.1]hept-2-yl]methyl]phenoxyl]heptanoic acid Following the procedure of Examples 23, 1 and 2 except substituting ethylbromoheptanoate for ethylbromoacetate and substituting phenylmesylate for hexylmesylate, the title compound is obtained.

EXAMPLE 27

(1α,2β,3β,4α)-[3-[[3-[2-(2-Butenyloxy)ethyl]-7-oxabicyclo[2.2.1]hept-2-yl]methyl]phenoxy]hexanoic acid Following the procedure of Examples 23, 1 and 2 except substituting ethylbromohexanoate for ethylbromoacetate and substituting 2-butenylmesylate for hexylmesylate, the title compound is obtained.

EXAMPLE 28

(1α,2β,3β,4α)-[3-[[3-[2-(3-Butenyloxy)ethyl]-7-oxabicyclo[2.2.1]hept-2-yl]methyl]phenoxy]octanoic acid Following the procedure of Examples 23, 1 and 2 except substituting ethylbromooctanoate for ethylbromoacetate and substituting 3-butenylmesylate for hexylmesylate, the title compound is obtained.

EXAMPLE 29

(1α,2β,3β4α)-[4-[[3-[2-(1-Pentenyloxy)ethyl]-7-oxabicyclo[2.2.1]hept-2-yl]methyl]phenoxy]acetic acid Following the procedure of Examples 23, 1 and 2 except substituting 4-bromophenylmethoxymethyl ether for 3-bromophenylmethoxymethyl ether and substituting 1-pentenylmesylate for hexylmesylate, the title acid is obtained.

EXAMPLE 30

(1α,2β,3β,4α)-2-[[3-[2-(Cycloheptyloxy)ethyl]-7-oxabicyclo[2.2.1]hept-2-yl]methyl]phenoxy]acetic acid Following the procedure of Examples 23, 1 and 2 except substituting 2-bromophenylmethoxymethyl ether for 3-bromophenylmethoxymethyl ether and substituting cycloheptylmesylate for hexylmesylate, the title acid is obtained.

EXAMPLE 31

(1α,2β,3β,4α)-[2-[[3-[2-(Pentyloxy)ethyl]-7-oxabicyclo[2.2.1]hept-2-yl]methyl]phenoxyl]acetic acid Following the procedure of Examples 23, 1 and 2 except substituting 2-bromophenylmethoxymethyl ether for 3-bromophenylmethoxymethyl ether and substituting pentyl tosylate for hexyl mesylate, the title acid is obtained.

EXAMPLE 32

(1α,2β,3β,4α)-[3-[[3-[3-(Hexyloxy)propyl]-7-oxabicyclo[2.2.1]hept-2-yl]methyl]phenoxy]acetic acid Following the procedure of Example 23 and Example 2 except in carrying out the Example 23, Part O step, substituting the Example 23 Part O aldehyde for the Example 23 Part N aldehyde to form (1α,2β,3β,4α)-[3-[[3-(3-oxo)propyl]-7-oxabicyclo[2.2.1]hept-2-yl]methyl]phenoxy]acetic acid, methyl ester and using the latter compound in the remainder of the Examples 23 and 2 procedure, the title compound is obtained.

EXAMPLE 33

(1α,2β,3β,4α)-[3-[[3-[4-(Hexyloxy)butyl]-7-oxabicyclo[2.2.1]hept-2-yl]methyl]phenoxy]acetic acid Following the procedure of Examples 23, 32 and 2 except in carrying out the Example 23, Part O step, substituting (1α,2β,3β,4α)-[3-[[3-(3-oxo)propyl]-7-oxabicyclo[2.2.1]hept-2-yl]methyl]phenoxy]acetic acid, methyl ester (prepared in Example 32) for the Example 23 Part O aldehyde, the title compound is obtained.

EXAMPLE 34

(1α,2β,3β,4α)-[3-[[3-[2-(Hexyloxy)ethyl]-7-oxabicyclo[2.2.1]hept-2-yl]ethyl]phenoxy]acetic acid

A.

(1α,2β,3β,4α)-[3-[[3-(2-Hydroxyethyl)-7-oxabicyclo[2.2.1]hept-2-yl]ethyl]phenyl]methoxymethyl ether Following the procedure of Example 1, Parts F to J except substituting (1α,2β,3β,4α)-[cis-exo-3-isopropyloxycarbonyloxymethyl-7-oxabicyclo[2.2.1]hept-2-yl]acetaldehyde (prepared in Example 4A) for the Example 1, Part E aldehyde, the title compound is obtained.

B.

(1α,2β,3β,4α)-[3-[[3-Formyl-7oxabicyclo[2.2.1]hept-2-yl]ethyl]phenyl]methoxymethyl ether To a solution of 960 mg of title A alcohol (3 mmole) in 20 ml of dry methylene chloride is added with stirring 1.3 g of pyridinium chlorochromate (6 mmole) and 1 g of fused sodium acetate. The reaction mixture is stirred at room temperature for several hours, whereupon it is diluted with ether and filtered through florisil. The filtrate is concentrated under reduced pressure to obtain title aldehyde.

C.

(1α,2β,3β,4α)-[3-[[3-(2-Oxo)ethyl]-7-oxabicyclo[2.2.1]hept-2-yl]ethyl]phenyl]methoxymethyl ether To a suspension of 2.055 g of methoxymethylenetriphenylphosphonium chloride (6 mmole, dried at 80° C. under vacuum for 2 hours) in 25 ml of dry toluene is added with stirring at 0° C., 2.6 ml of a 1.55M solution of K-t-amylate in toluene (4 mmole) dropwise. The red solution is stirred at 0° C. for an additional 1 hour, whereupon a solution of 636 mg of title B aldehyde (2 mmole) in 10 ml of dry toluene is added dropwise over a period of 30 minutes at 0° C. A few minutes after the addition is complete, the reaction mixture is quenched by addition of glacial acetic acid.

The reaction mixture is poured into saturated ammonium chloride solution and extracted with ether. The combined ether extract is dried over anhydrous magnesium sulfate and concentrated in vacuo. The crude residue is triturated with ether to remove the precipitated phosphine oxide. Chromatography on an LPS-1 silica gel column and elution with 10–40% ethyl acetate in hexane affords the enol-ether.

The purified enol-ether is dissolved in 10 ml of THF and to this is added 20 ml of a 20% aqueous trifluoroacetic acid solution. The resulting bi-phasic solution is stirred at room temperature for several hours, whereupon solid NaHCO$_3$ is added to the reaction mixture to adjust the pH to ~7. The reaction mixture is now extracted thoroughly with methylene chloride. The combined methylene chloride extract is dried over anhydrous magnesium sulfate and concentrated in vacuo to afford the title aldehyde.

D.

(1α,2β,3β,4α)-[3-[[3-(2-Hydroxyethyl)-7-oxabicyclo[2.2.1]hept-2-yl]ethyl]phenyl]methoxymethyl ether To a solution of 332 mg of title C aldehyde (1 mmole) in 10 ml of absolute ethanol at 0° C. is added with stirring 40 mg of sodium borohydride (~1 mmole). The reaction mixture is stirred at 0° C. for 1 hour, whereupon it is poured into 1N aqueous hydrochloric acid solution and extracted thoroughly with methylene chloride. The methylene chloride extract is dried over anydrous magnesium sulfate and concentrated under reduced pressure to afford the desired title alcohol.

E.

(1α,2β,3β,4α)-[3-[[3-[2-(Hexyloxy)ethyl]-7-oxabicyclo[2.2.1]hept-2-yl]ethyl]phenoxy]acetic acid Following the procedure of Examples 1K to M and Example 2 except substituting the above Part D alcohol for the Example 1, Part J alcohol, the title compound is obtained.

EXAMPLE 35

(1α,2β,3β,4α)-[3-[[3-[(2-(Benzyloxy)ethyl]-7-oxabicyclo[2.2.1]hept-2-yl]ethyl]phenoxy]butanoic acid Following the procedure of Examples 34, 1 and 2 except substituting ethylbromobutanoate for ethylbromoacetate and substituting benzyl tosylate for hexyl mesylate, the title compound is obtained.

EXAMPLE 36

(1α,2β,3β,4α)-[3[[3-[(2-Cyclohexylmethyloxy)ethyl]-7-oxabicyclo[2.2.1]hept-2-yl]ethyl]phenoxy]pentanoic acid Following the procedure of Examples 34, 1 and 2 except substituting ethylbromopentanoate for ethylbromoacetate and substituting cyclohexylmethyl mesylate for hexyl mesylate, the title compound is obtained.

EXAMPLE 37

(1α,2β,3β,4α)-[3-[[3-[(2-Phenyloxy)ethyl]-7-oxabicyclo[2.2.1]hept-2-yl]ethyl]phenoxy]heptanoic acid Following the procedure of Examples 34, 1 and 2 except substituting ethylbromoheptanoate for ethylbromoacetate and substituting phenylmesylate for hexylmesylate, the title compound is obtained.

EXAMPLE 38

(1α,2β,3β,4α)-[3-[[3-[2-(2-Butenyloxy)ethyl]-7-oxabicyclo[2.2.1]hept-2-yl]ethyl]phenoxy]hexanoic acid Following the procedure of Examples 1 and 2 except substituting ethylbromohexanoate for ethylbromoacetate and substituting 2-butenylmesylate for hexylmesylate, the title compound is obtained.

EXAMPLE ⇌

(1α,2β,3β,4α)-[3-[[3-[2-(3-Butenyloxy)ethyl]-7-oxabicyclo[2.2.1]hept-2-yl]ethyl]phenoxy]octanoic acid Following the procedure of Examples 34, 1 and 2 except substituting ethylbromooctanoate for ethylbromoacetate and substituting 3-butenylmesylate for hexylmesylate, the title compound is obtained.

EXAMPLE 40

(1α,2β,3β,4α)-[4-[[3-[2-(1-Pentenyloxy)ethyl]-7-oxabicyclo[2.2.1]hept-2-yl]ethyl]phenoxy]acetic acid Following the procedure of Examples 34, 1 and 2 except substituting 4-bromophenylmethoxymethyl ether for 3-bromophenylmethoxymethyl ether and substituting 1-pentenylmesylate for hexylmesylate, the title acid is obtained.

EXAMPLE 41

(1α,2β,3β,4α)-[2-[[3-[(2-Cycloheptyloxy)ethyl]-7-oxabicyclo[2.2.1]hept-2-yl]ethyl]phenoxy]acetic acid Following the procedure of Examples 34, 1 and 2 except substituting 2-bromophenylmethoxymethyl ether for 3-bromophenylmethoxymethyl ether and substituting cycloheptylmesylate for hexylmesylate, the title acid is obtained.

EXAMPLE 42

(1α,2β,3β,4α)-[2-[[3-[2-(Pentyloxy)ethyl]-7-oxabicyclo[2.2.1]hept-2-yl]ethyl]phenoxy]acetic acid Following the procedure of Examples 34, 1 and 2 except substituting 2-bromophenylmethoxymethyl ether for 3-bromophenylmethoxymethyl ether and substituting pentyl tosylate for hexyl mesylate, the title acid is obtained.

EXAMPLE 43

(1α,2β,3β,4α)-[3-[[3-(Hexyloxy)propyl]-7-oxabicyclo[2.2.1]hept-2-yl]propyl]phenoxy]acetic acid Following the procedure of Examples 34, 1 and 2 except substituting the Example 34 Part A aldehyde for the Example 1 Part E aldehyde in carrying out the procedure of Example 1 Part F and substituting the example 34 Part D alcohol for the Example 34 Part A alcohol in carrying out the procedure of Example 34 Part B, the title compound is obtained.

What is claimed is:

1. A compound having the structural formula

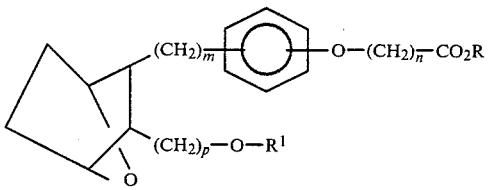

and including all stereoisomers thereof;
wherein m is 1 to 4; n is 1 to 8; p is 1 to 4; R is H, lower alkyl or alkali metal; and $R^1$ is lower alkyl, aryl, aralkyl, cycloalkyl, cycloalkylalkyl or lower alkenyl, wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;
the term aryl by itself or as part of another group contains 6 to 10 carbons and is unsubstituted or substituted with 1 or 2 lower alkyl groups 1 or 2 halogen groups and/or 1 or 2 lower alkoxy groups;
the term cycloalkyl by itself or as part of another group contains 3 to 12 carbons and is unsubstituted or substituted with 1 or 2 halogens, 1 or 2 lower alkyl groups and/or 1 or 2 lower alkoxy groups;
the term lower alkenyl by itself or as part of another group contains 2 to 12 carbons;
the terms $(CH_2)_m$ and $(CH_2)_p$ include 1 to 4 carbons in the normal chain and the term $(CH_2)_n$ includes 1 to 8 carbons in the normal chain;
and the terms $(CH_2)_m$ $(CH_2)_n$ and $(CH_2)_p$ may be unsubstituted or include one or more lower alkyl substituents.

2. The compound as defined in claim 1 wherein m is 1 and n is 1.

3. The compound as defined in claim 1 wherein p is 1.

4. The compound as defined in claim 1 having the formula

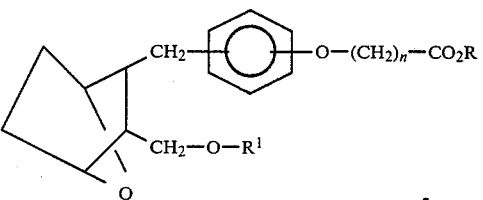

wherein R is hydrogen and $R^1$ is lower alkyl, including all stereoisomers thereof.

5. The compound as defined in claim 4 wherein $R^1$ is butyl, pentyl, hexyl, heptyl or 1,1-dimethylpentyl.

6. The compound as defined in claim 1 having the name (1α,2β,3β,4α)-[3-[[3-[(hexyloxy)methyl]-7-oxabicyclo[2.2.1]hept-2-yl]methyl]phenoxy]acetic acid or the methyl or ethyl ester thereof, including all stereoisomers thereof.

7. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

8. The method as defined in claim 7 wherein said compound is administered in an amount within the range of from about 1 to about 100 mg/kg.

9. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

10. A method of inhibiting bronchoconstriction associated with asthma, which comprises administering to a mammalian host an effective amount of a compound as defined in claim 1 or a pharmaceutically acceptable salt thereof.

11. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,536,513
DATED : August 20, 1985
INVENTOR(S) : Jagabandhu Das et al.

It is certified that error appears in the above-identified patent and that said Letters Patent is hereby corrected as shown below:

Column 7, line 1, "either" should read --ether--.
Column 11, structures Ib, Ic and Id should read as follows:

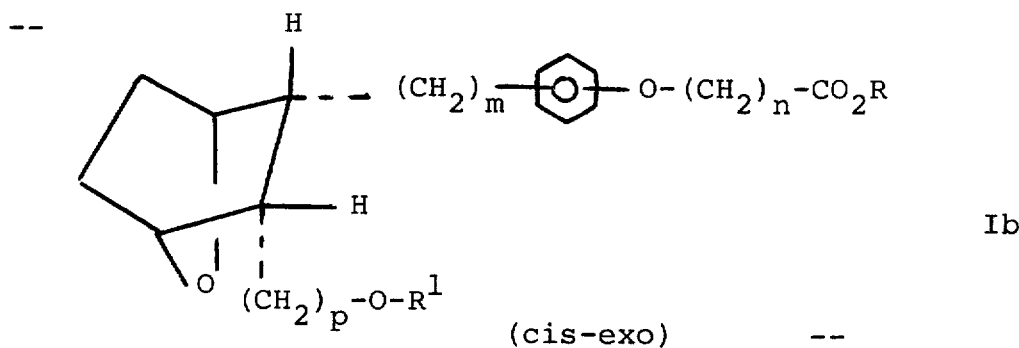

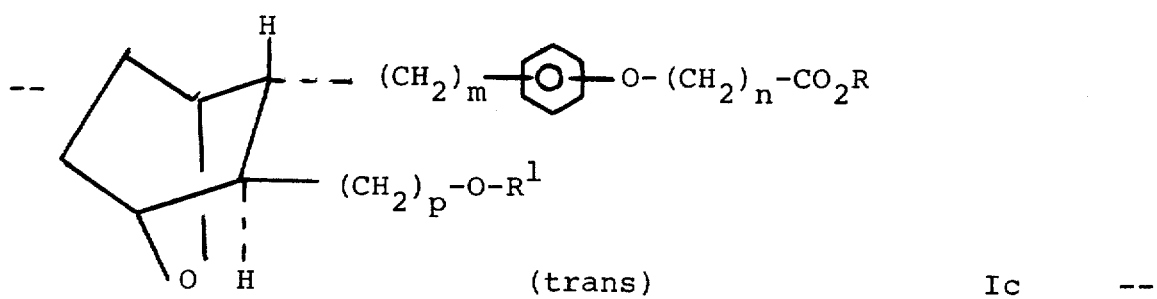

UNITED STATES PATENT AND TRADEMARK OFFICE
CERTIFICATE OF CORRECTION

PATENT NO. : 4,536,513
DATED : August 20, 1985
INVENTOR(S) : Jagabandhu Das et al.

It is certified that error appears in the above-identified patent and that said Letters Patent is hereby corrected as shown below:

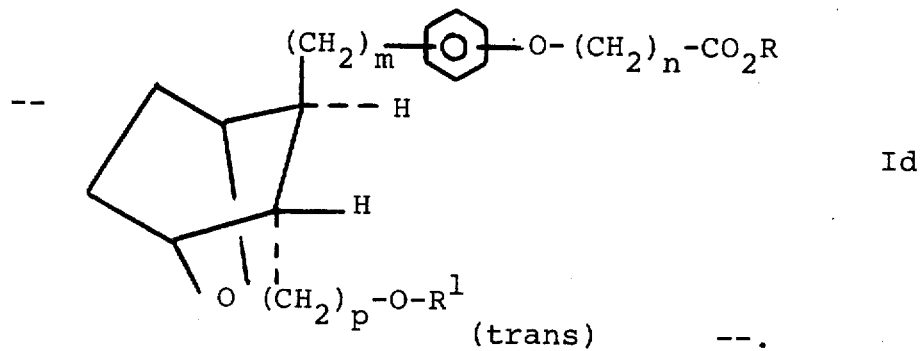

Column 12, line 8, "stiffnes" should read --stiffness--.
Column 13, line 25, "20.6" should read --20.5--.
Column 13, line 55, "$MgSO_2$" should read --$MgSO_4$--.
Column 14, line 24, "54" should read --4--.
Column 25, line 31, the Example No. should read --Example 39--.

UNITED STATES PATENT AND TRADEMARK OFFICE
CERTIFICATE OF CORRECTION

PATENT NO. : 4,536,513

DATED : August 20, 1985

INVENTOR(S) : Jagabandhu Das et al.

It is certified that error appears in the above-identified patent and that said Letters Patent is hereby corrected as shown below:

Column 26, line 60, the formula in Claim 4 should read

-- 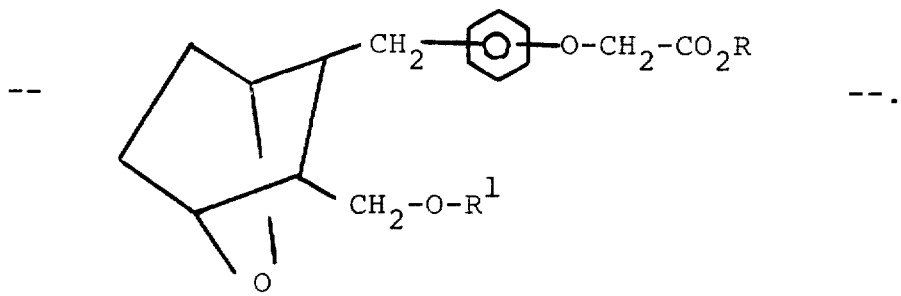 --.

Signed and Sealed this

Twenty-eighth Day of October, 1986

[SEAL]

Attest:

DONALD J. QUIGG

Attesting Officer     Commissioner of Patents and Trademarks